United States Patent [19]

Takeuchi et al.

[11] Patent Number: 4,983,636
[45] Date of Patent: Jan. 8, 1991

[54] COMPOSITION AND METHOD OF TREATING SELECTED MALIGNANT CONDITIONS

[75] Inventors: Setsuo Takeuchi, Higashiyamato; Mutsuyuki Kochi, Matsudo, both of Japan

[73] Assignees: Rikagaku Kenkyusho Wako, Wako; Mutsuyuki Kochi, Matsudo, both of Japan

[21] Appl. No.: 265,415

[22] Filed: Oct. 31, 1988

Related U.S. Application Data

[63] Continuation of Ser. No. 44,795, Apr. 30, 1987, abandoned, and Ser. No. 720,538, Apr. 8, 1985, abandoned, which is a continuation of Ser. No. 573,592, Jan. 25, 1984, abandoned, which is a continuation of Ser. No. 508,987, Jun. 28, 1983, abandoned, which is a continuation of Ser. No. 296,994, Aug. 27, 1981, abandoned, which is a continuation of Ser. No. 84,540, Oct. 15, 1979, abandoned, which is a continuation of Ser. No. 942,402, Sep. 14, 1978, abandoned, which is a continuation of Ser. No. 774,867, Mar. 7, 1977, abandoned.

[30] Foreign Application Priority Data

Mar. 9, 1976 [JP] Japan .................................. 51-25225

[51] Int. Cl.$^5$ .................... A61K 31/11; A61K 31/715
[52] U.S. Cl. ........................................ 514/699; 514/58
[58] Field of Search ................................. 514/699, 58

[56] References Cited

U.S. PATENT DOCUMENTS 2,827,452  3/1958  Schlenk et al. .................... 536/103

OTHER PUBLICATIONS

Dyer, An Index of Tumor Chemotherapy, WIH, pp. 10–12 and 99 (1949).

*Primary Examiner*—Jerome D. Goldberg
*Attorney, Agent or Firm*—Bucknam and Archer

[57] ABSTRACT

As a result of research work and investigations relating to the effect of benzaldehyde on cell membranes, it was found that benzaldehyde has high activity in the treatment of selected malignant conditions. Based on this finding, we have now completed the present invention directed to a composition comprising benzaldehyde as the active ingredient. This composition is effective against selected malignant conditions which are carcinoma of the colon, cancer of the stomach, cancer of the tongue, peritonitis carcinomatosa, cancer of the liver and malignancies induced by $SF_{40}$ virus.

14 Claims, 4 Drawing Sheets

COMPOSITION AND METHOD OF TREATING SELECTED MALIGNANT CONDITIONS

This application is a Continuation of U.S. Ser. No. 044,795, filed Apr. 30, 1987 and U.S. Ser. No. 720,538 filed Apr. 8, 1985. U.S. Pat. No. 720,538 was a Continuation of U.S. Ser. No. 573,592 filed Jan. 25, 1984, which was a Continuation of U.S. Ser. No. 508,987 filed June 28, 1983, which was a Continuation of U.S. Ser. No. 296,994 filed Aug. 27, 1981, which was a Continuation of U.S. Ser. No. 084,540 filed Oct. 15, 1979, which was a Continuation of U.S. Ser. No. 942,402 filed Sept. 14, 1978, which was a Continuation of U.S. Ser. No. 774,867 filed Mar. 7, 1977. All these applications have been abandoned.

FIELD OF INVENTION:

The present invention relates to a composition containing benzaldehyde as the active ingredient. The term "carcinostatic" as used herein refers to a composition effective against selected malignant conditions which are carcinoma of the colon, cancer of the stomach, cancer of the tongue, peritonitis carcinomatosa, cancer of the liver and malignancies induced by $SV_{40}$ virus.

As the carcinostatic agent, there have heretofore been used antibiotic carcinostatic agents such as mitomycin and bleomycin, vegetable substances such as vincristine and PSK and synthetic carcinostatic agents such as nitrogen mustard, 5-fluorouracil (5-FU) and Futraful. Most of these known carcinostatic agents have been developed as agents having a selective cytotoxicity, namely as agents for controlling cancer by directly attacking malignant cells. Accordingly, they naturally act on normal cells, are highly toxic and produce unfavorable and serious side effects. On the other hand, PSK is polysaccharide extracted from mushrooms and it is said that it has an effect of increasing immunity in the host. Although PSK has a considerable effect on leukaemia, it has almost no substantial effect on other cancers. Thus, conventional agents cannot be used as decisive chemotherapeutic agents for cancers, but they are merely used in combination with other agents or as auxiliary agents for surgical operations or radiotherapy. Recently, the role of methylglyoxal has attracted attention. It is said that methylglyoxal is broadly distributed in mammalian cells and participates in growth and differentiation of cells. Based on the fact that the concentration of methylglyoxal is decreased in malignant cells, attempts have been made to normalize malignant cells by controlling the activity of glyoxalases which inactivates methylglyoxal and reserch work and investigation have been made to discover glyoxalase inhibitors.

The present inventors have conducted research work on the relation between the effect of benzaldehyde on cell membranes and the activity of benzaldehyde.

As a result, we have found that benzaldehyde is effective for controlling tumor cells of mice, and have now completed the present invention of a composition comprising benzaldehyde as the active ingredient.

At present, benzaldehyde is used as a material for chemical synthesis, and is used only as a flavoring agent for commercial use.

Further, no references relating to the activity of benzaldehyde can be found.

The composition of the present invention probably does not attack tumor cells directly, but it has a specific activity and exerts a therapeutic effect according to a mechanism quite different from the therapeutic mechanism heretofore considered for conventional chemotherapeutic agents.

The mechanism through which benzaldehyde, the active ingredient of the composition of the present invention, acts has not been completely elucidated. It is known that tumor cells are characterized by changes in the membrane structure and the tumor cells per se are very active and rapidly incorporate various essential substrates. It is believed that benzaldehyde has influences on the membranes of cells.

For example, when *Escherichia coli* is allowed to incorporate radioactive tryptophane, if benzaldehyde is present, the incorporation is promoted but incorporation of nucleic acids and other amino acids is inhibited by the presence of benzaldehyde. Thus, benzaldehyde has selective influences of the substrate transformation systems characteristics of *Escherichia coli*.

Therefore, it is apparent that benzaldehyde has affects the properties of cell membranes, and it is construed that this specific property of benzaldehyde is closely concerned with the activity for some reasons or other.

Results of the tests made to examine the influence of benzaldehyde on the uptake of various amino acids and nucleic acid bases by using *Escherichia coli* will now be described in detail.

More specifically, *E. coli* W 3110 and *E. coli* S were cultured according to the scheme described below, and the effect of benzaldehyde on the uptake of amino acids and nucleic acid bases (thymine, adenine, glutamic acid, alanine and tryptophan) used as substrates by cell membranes was examined.

Table 1 shows a flow chart of the experimental steps of the process in which *E. coli* W 3110 and *E. coli* S were cultured and cells including the substrate and benzaldehyde were recovered. In the Table, "glucose" was added as an energy source for cells in which propagation had been terminated and "CM" (Chloramphenicol) was added so as to terminate propagation of cells. Further, "14C-substrate" means a substrate labelled by a 14C-labelling compound and "Ba" stands for benzaldehyde having various concentrations. Separately, instead of this composition of the foregoing additives, a composition comprising glucose, CM, 14C-substrate and colistin was added and cells were similarly obtained. The colistin was added for a comparison system to the Ba-added system because colistin is a permeation inhibitor for cell membranes (antibiotic substance).

TABLE I

E. COLI (W3110, S)

37° C. OVER NIGHT
IN CASAMINO ACID OR CR MED.

PRECULTURED CELLS (0.3 ML)

37° C. UNTIL OD660 0.3
IN 30 ML OF SAME MED.
HARVESTED ON MEMBRANE FILT.
WASHED WITH TRIS-HCL (PH 7.35)

HARVESTED CELLS

TABLE I-continued

```
SUSPENDED IN V&B OR CR MED.
        ⎧ GLUCOSE    0.2%
ADDED   ⎨ CM         30 OR 40 MCG/ML
        ⎩ 14 C-SUBST. 0.1 OR 0.2 μCI/ML
          BA

37° C. 30 MIN.
COLLECTED ON MEMBRANE FILT.
WASHED WITH TRIS BUFFER
CELLS
   │
   │COUNTING
```

The influence of benzaldehyde on the uptake of respective substrates by cells was examined to obtain the results shown in Table 2.

In Table 2, the value of each numerator means a value measured by a scintillation counter and the value of each denominator means a ratio (%) to the value of the control (100%).

From the results shown in Table 2, it will readily be understood that the presence of benzaldehyde specifically promotes the uptake of tryptophane, while it exerts an uptake inhibiting action in the case of other substrates.

TABLE 2

EFFECT OF BENZALDEHYDE ON AMINO ACIDS AND BASES UPTAKE

| | | | | INCORPORATION (CPM %) | | |
|---|---|---|---|---|---|---|
| | | | COLISTIN | BENZALDEHYDE | | |
| STRAIN | SUBSTRATE | CONTROL | 5 PPM | $10^{-1}$ PPM | $10^{-2}$ PPM | $10^{-3}$ PPM |
| E. COLI, W3110 | THYMINE | 2028/100 | 333/16 | 1399/69 | 1566/77 | 1891/93 |
| | ADENINE | 4433/100 | 1066/23 | 3135/71 | 3684/83 | 4246/96 |
| | GLUTAMIC ACID | 4067/100 | 670/16 | 2842/70 | 2779/68 | 3203/79 |
| | ALANINE | 6072/100 | 1009/17 | 5283/87 | 5438/90 | 5838/96 |
| E. COLI, S | TRYPTOPHANE | 680/100 | 439/65 | 1076/158 | 915/134 | 808/119 |

Figure 1A:
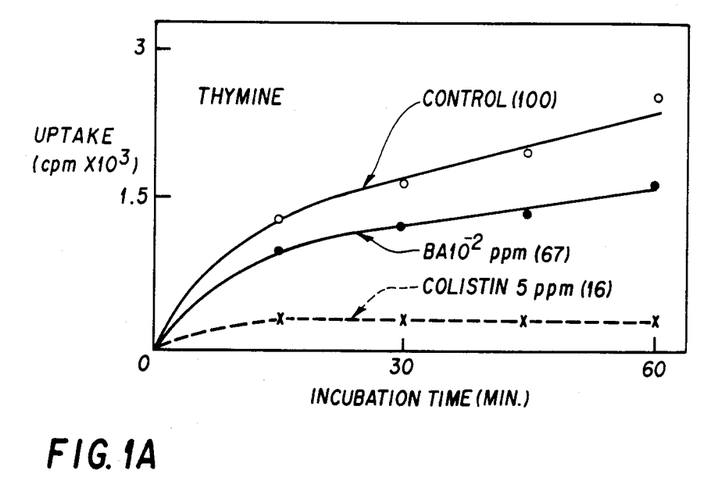
FIG. 1 is a graph illustrating the effect of benzaldehyde on the changes in nucleic acid bases uptake in cells of *Escherichia coli* with the lapse of time.
Figure 1B:
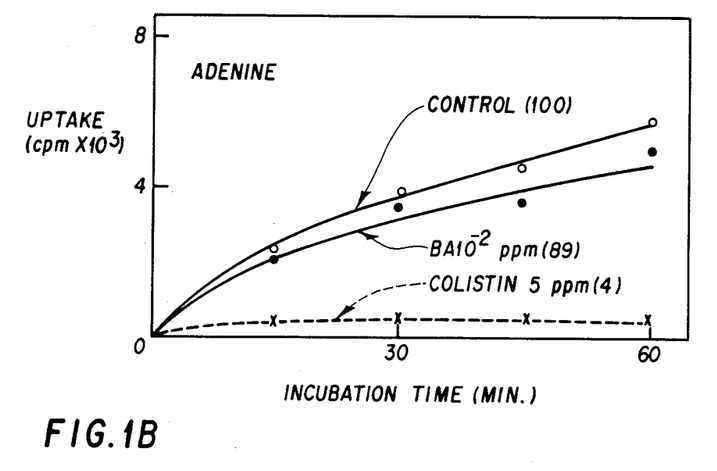
Figure 2A:
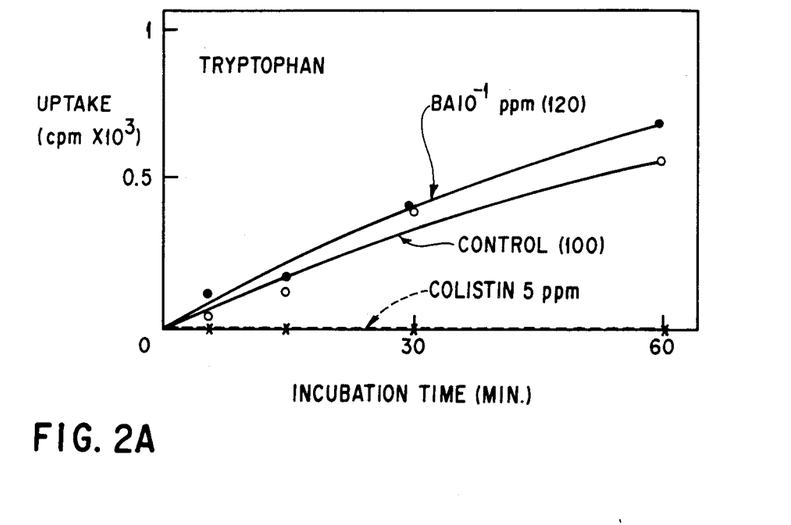
FIG. 2 is a graph illustrating the effect of benzaldehyde on the changes in amino acids uptake in cells of *Escherichia coli* with the lapse of time.
Figure 2B:
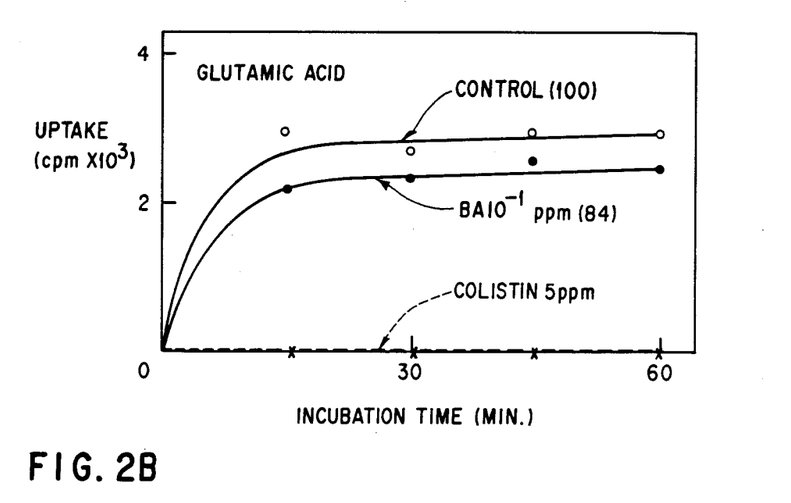

Results of the examination made on the effect of benzaldehyde on changes in the incorporated nucleic acid bases with the lapse of time are shown in FIG. 1, and the results of examination made on the effect of benzaldehyde on changes in the incorporated amine acids with the lapse of time are shown in FIG. 2, from which it is seen that the uptake of tryptophane increases with the lapse of time.

Figure 3A:
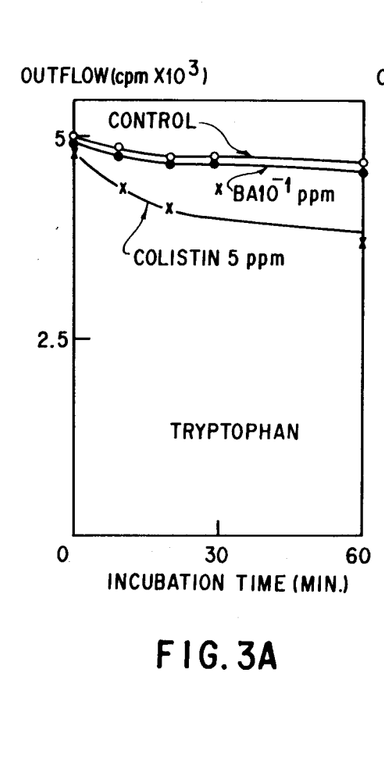
FIG. 3 is a graph illustrating the effect of benzaldehyde on outflow from cells in amino acids and nucleic acid bases uptaken by cells of *Escherichia coli*.
Figure 3B:
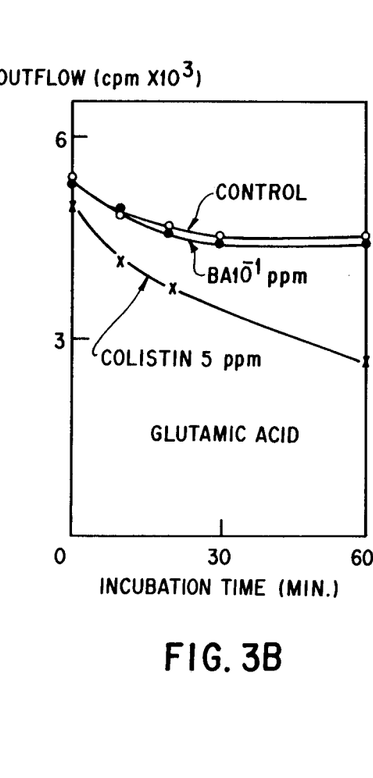
Figure 3C:
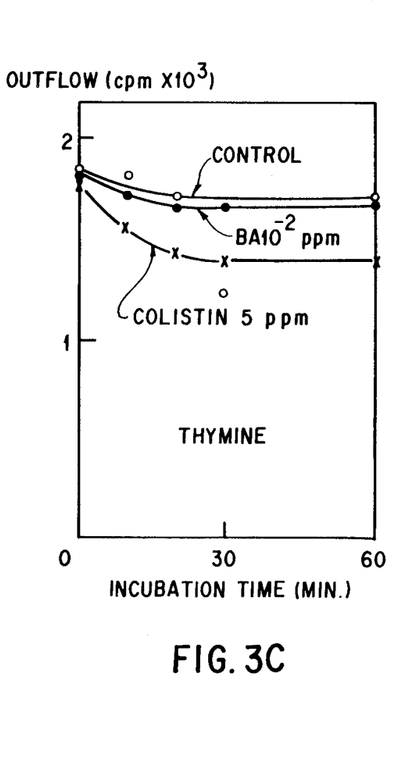

Results of the examine made on the effect of benzaldehyde on outflow of incorporated substrates from cells are shown in FIG. 3, from which it is seen that in the colistin-added system, cell membranes are destroyed and outflow of the substrate is extreme, whereas in the benzaldehyde-added system, outflow of the substrate is remarkably reduced and is not changed from outflow of the substrate in the control system, and that benzaldehyde causes no damage to cell membranes.

Incidentally, FIG. 3 illustrates results obtained when a substrate free of benzaldehyde was added in advance to cells. The cells were incubated in a culture medium in which benzaldehyde had been treated, and the substrate which flowed out of the cells was measured.

From the foregoing results, it is seen that benzaldehyde specifically promotes the uptake of tryptophane among substrates, and this fact suggests that benzaldehyde participates in the active transportation system of cell membranes.

In general, Ehrlich ascites tumor is highly sensitive to conventional carcinostatic agents of cytotoxic type, and Ehrlich solid tumor is relatively lowly sensitive to most of these known carcinostatic agents. In contrast, the active ingredient of the composition of the present invention acts strongly on the solid tumor rather than the ascites tumor. Namely, the active ingredient of the present invention is characterized in that it has a prominent effect on Erlich solid tumor as illustrated in Test 3 given hereinafter. The toxicity of benzaldehyde as an active ingredient, i.e., $LD_{sc}$, is 5 g/kg in case of subcutaneous injection to rats. Further, since benzaldehyde has a low-molecular-weight structure, it is promptly extracted from living bodies and causes no side effects. Moreover, when benzaldehyde is administered continuously for 10 days, bad influences such as toxicity are not imposed on the host with daily doses up to 200 mg/Kg. Still in addition, benzaldehyde has a broad region of effective concentrations and it has now been confirmed by clinical experiments that malignant cells of adenomatous carcinoma, squamous cell carninoma, sarcoma and the like, especially undifferentiated tumors, are highly sensitive to benzaldehyde. Still further, benzaldehyde is expected to be effective for controlling blood selected malignant conditions such as leukaemia because benzaldehyde is effective against lymphosarcoma. Thus, the composition of the present invention is very unique in the point that it is efficacious against a broadrange of carcinomatous diseases.

As will readily be understood from the foregoing illustration, the composition of the present invention has high safety and exerts an excellent therapeutic effect on a broad range of diseases. Therefore, it is believed that the composition of the present invention is a very excellent chemotherapeutic agent.

In pharmaceutical preparations of the composition of the present invention, benzaldehyde as the active ingredient may be formed into aqueous or oily suspensions, solutions or emulsion which are used for subcutaneous or intravenous injection and transfusion. Further, benzaldehyde may be formed into preparations suitable for oral administration, for example, enteric capsules. Benzaldehyde may be used in the form of an inclusion compound of benzaldehyde in β- or γ-cyclodextrin.

The inclusion compound may be formed into enteric capsules and tablets, and these capsules and tablets can be effectively used.

SUMMARY OF THE INVENTION

It is therefore a primary object of the present invention to provide a composition comprising benzaldehyde as the active ingredient.

Another object of the present invention is to provide a medicinal preparation suitable for administering benzaldehyde as an agent against selected malignant conditions.

Still another object of the present invention is to provide a method for treating selected malignant conditions by administrating a composition comprising benzaldehyde.

Other objects and advantages of the present invention will be apparent from the description of the specification and claims.

DESCRIPTION OF THE PREFERRED EMBODIMENTS

The present invention will now be described in detail.

The composition of the present invention comprises benzaldehyde as the active ingredient.

The composition of the invention may be formed into various pharmaceutical preparations such as for injection, transfusion and oral administration as detailed hereinafter, and suitable preparation forms may be decided appropriately depending on the intended administration method.

Namely, water-soluble liquid and oil preparations for injection and transfusion may be formed by using benzaldehyde as the effective ingredient according to ordinary methods adopted in the pharmaceutical industry, and preparations for oral administration, such as capsules and tablets, may also be formed according to methods ordinarily adopted in the pharmaceutical industry.

The activity, acute toxicity and other properties of benzaldehyde will now be described.

(1) Activity

Test 1

As the experimental animal, there were used four mice of the first filial generation of C57BL/6 and DBA/2, which were 6 to 7 weeks old. A carcinoma (Adeno-carcinoma 755) was implanted on the hypoderm in the back by using an implanting needle. When 24 hours had passed from the implantation, 0.5 to 1.0 ml of a 10 ppm suspension of purified benzaldehyde in a physiological sodium chloride solution was subcutaneously injected. This treatment was conduced once a day for 9 days. On the 11th day from the implantation, the weight of the tumor was measured with respect to each group to obtain the results shown in Table 3.

TABLE 3

|  | Tumor Weight (g) | | | Average Weight (g) | Relative Weight (%) |
| --- | --- | --- | --- | --- | --- |
| Control Group | 6.1 | 5.5 | 5.8 | 5.8 | 100 |
| Treated Group | 4.6 | 2.6 | 4.1 | 3.8 | 65.5 |

Test 2

According to the same procedures as described in Test 1, a 3.5% suspension of purified benzaldehyde in a 30% aqueous solution of glycerin containing Tween 80 was intraperitoneally injected in an amount of 0.1 ml of the suspension once a day. The treatment was continued for 9 days. On the 11th day from the implantation, the tumor weight was measured with respect to each group to obtain results shown in Table 4.

TABLE 4

|  | Tumor Weight (g) | | | | Average Weight (g) | Relative Weight (%) |
| --- | --- | --- | --- | --- | --- | --- |
| Control Group | 7.0 | 5.6 | 3.8 | 7.2 | 5.90 | 100 |
| Treated Group | 3.3 | 3.4 | 4.0 | 3.5 | 3.55 | 60 |

Test 3

Ten mice of RFVL which were 4 to 5 weeks old were used as the experiemental animals, and about $10^6$ cells/0.2 ml of Ehrlich carcinoma were implanted subcutaneously at the right armpit. When 24 hours had passed, 0.25 ml of a 1000 ppm suspension of purified benzaldehyde in a biological sodium chloride solution (corresponding to a dose of 10 mg/Kg of the body weight) was intraperitoneally injected once a day. This treatment was continued for 9 days. On the 11th day from the tumor implantation, the tumor weight was measured with respect to each group to obtain results shown in Table 5. In each of control and treated groups, the increase of the body weight in the tested mice during the test was 3.5 g as the average value determined on 10 mice.

TABLE 5

|  | Tumor Weight (g) | | | | | | | | | | Average Weight (g) | Relative Weight (%) |
| --- | --- | --- | --- | --- | --- | --- | --- | --- | --- | --- | --- | --- |
| Control Group | 9.0 | 4.2 | 3.4 | 2.6 | 2.5 | 2.4 | 1.2 | 1.1 | 1.0 | 0.5 | 2.79 | 100 |
| Treated Group | 3.8 | 2.4 | 2.2 | 0.8 | 0.8 | 0.6 | 0.6 | 0.5 | 0.4 | 0.3 | 1.24 | 44 |

Test 4

Ten mice of RFVL which were 4 to 5 weeks old were used as the test animals and about $10^6$ cells/0.2 ml of Ehrlich carcinoma were implanted intraperitoneally. When 24 hours had passed from the inoculation, administration of a suspension of purified benzaldehyde in a 0.85% biological sodium chloride solution was started, and the treatment was continued for 10 days to examine the survival effect. As will be readily be understood from FIG. 4, the survival effect of 15.4% was obtained by intraperitoneal injection of the suspension at a dose of 50 mg/Kg of the body weight per day and the survival effect of 26.9% was obtained by intraperitoneal injection of the suspension at a dose of 100 mg/Kg of the body weight per day.

Figure 4:
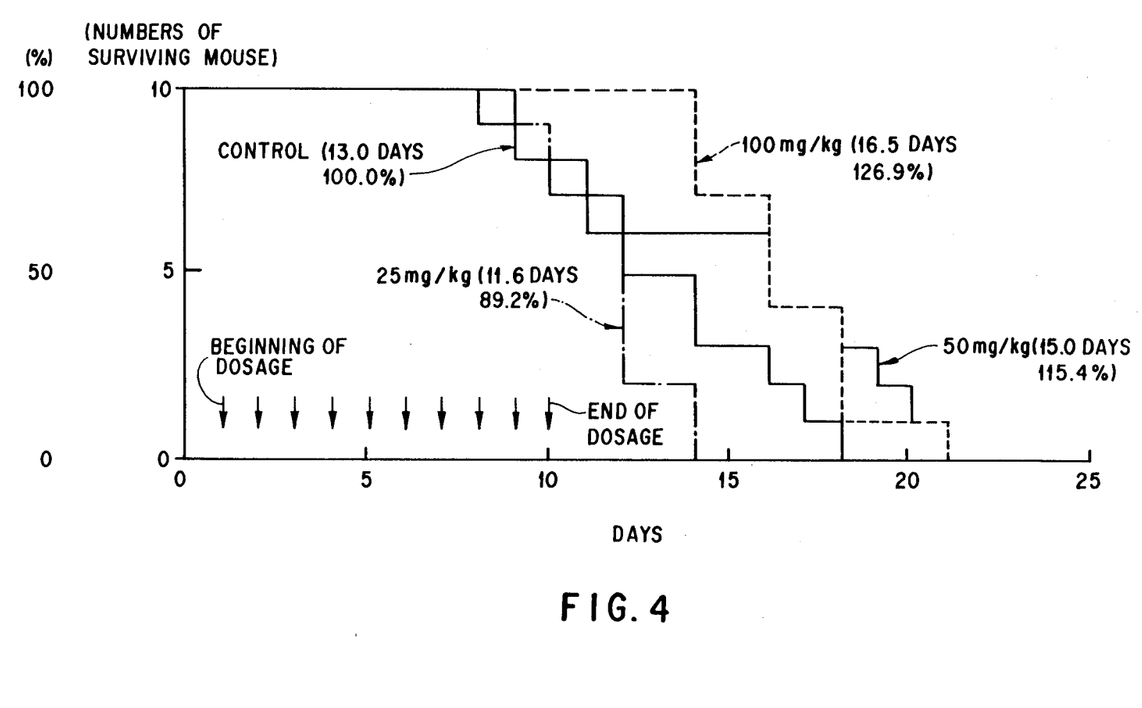
FIG. 4 is a graph illustrating the effect of benzaldehyde in terms of the surviving effect in tested mice.

In FIG. 4, the suspension was administered at doses of 25, 50 and 100 mg/Kg/day to treated groups and the 0.85% biological sodium chloride solution alone was administered to a control group. Parenthesized values shown for each group are average values of the number of living days and the survival ratio.

Test 5 (Clinical Experiment on the Human Body)

Hard, enteric capsules of an inclusion compound of benzaldehyde in β-cyclodextrin which were prepared according to the method described in Medicinal Preparation Example 4, were orally administered to a patient (male, 79 years old) suffering from a gigantic tumor of the later stage in the right pulmonatory hilum, who was extremely enfeebled, had no appetite and was perpetually troubled by intense pains in the area of the chest, nausea and a large volume of bloody phlegm.

Five capsules (each containing 100 mg of the inclusion compound of benzaldehyde) were administered at one time, and the administration was conduced 4 times per day. When 3 days had passed from the initial administration, the apparent condition of the patient had improved, and when 10 days had passed from the start of administration, the foregoing symptoms had moderated to a great extent and the patient was relieved of pains in the chest and nausea with a remarkable reduction in the excretion of bloody phlegm. Simultaneously, his appetite improved and other notable improvements were clinically observed.

When one month had passed from the initial administration, X-ray diagnosis was conduced, and it was found that the size of the tumor had remarkably decreased.

(2) Acute Toxicity

The acute toxicity of purified benzaldehyde, $LD_{sc}$ is 5 g/Kg on rats. Since it has a low-molecular-weight structure, it is promptly excreted from the living body. No toxicity is observed when benzaldehyde is continuously administered by intraperitoneal injection for 10 days at a daily dose of up to 200 mg/Kg.

The dosage and administration method of benzaldehyde will now be described.

There can be used commercially available purified benzaldehyde as the active ingredient.

Benzaldehyde may be aministered by intravenous injection and subcutaneous injection or may be orally administered in the form of capsules and tablets. The dosage for adults is varied to some extent depending on the administration course and frequency, but in general, a preferred daily dose is about 0.001 to about 10 mg/Kg of the body weight in case of aquatic preparation and about 0.005 to about 50 mg/Kg of the body weight in case of oral administration.

When benzaldehyde is formed into liquid preparations for injection and transfusion, it is provided in the form of ampoules containing a unit amount for administration or vessels containing a unit administration of benzaldehyde together with pharmaceutical additives. These preparations may be suspensions, solutions and emulsions in oily or aqueous vehicles, and additives such as suspending agents, stabilizers and dispersants may be incorporated into these preparations. As the suspending agent, there can be used, for example, glucose, gelatin and aluminum stearate gel, and as the stabilizer, there can be used, for example, lecithin, linolic acid and sorbitan mono-oleate. Further, non-aqueous vehicles, such as almond oil, coconut oil, refined sesame oil and oily esters and antiseptics such as methyl p-hydroxybenzoate and sorbic acid may be used.

In general, the preparation contains about 10 to 100 mg of benzaldehyde in 1000 ml of physiological saline solution.

When benzaldehyde is orally administered, it is preferred that it be administered in the form readily absorbable from the intestinal tract, for example, in the form of capsules.

Binders such as gelatin and sorbitol, excipients such as lactose, sucrose, starch and glycine, stabilizers such as magnesium stearate and ascorbic acid, and disintegration such as potato starch are optionally used for formation of capsules for oral administration. In general, the capsule contains about 5–50 mg of benzaldehyde.

Benzaldehyde may be used in the form of powder of an inclusion compound formed by including benzaldehyde in a cyclodextrin. This inclusion compound may be formed into enteric capsules and tablets, and these capsules and tablets can be effectively used.

β-cyclodextrin and γ-cyclodextrin may suitably be employed as the cyclodextrin, and the inclusion compound can be prepared by the saturated aqueous solution method or kneading method.

According to the saturated aqueous solution method, for example, a saturated aqueous solution of β-cyclodextrin is first prepared, and purified benzaldehyde is incorporated in the solution. The mixture is ordinarily agitated for 4 to 8 hours, whereby the inclusion compound is formed as a precipitate, According to the kneading method, a small amount of water is added to β-cyclodextrin to form a paste. and purified benzaldehyde to be included is added to the paste. The mixture is sufficiently kneaded by a mortar or crushing mixer to form a water-containing inclusion compound.

The so-prepared inclusion compound of benzaldehyde can be used as it is. However, in order to stabilize the inclusion compound, the obtained inclusion compound may be washed with a suitable solvent such as acetone or ethanol. By this washing treatment, non-included benzaldehyde is removed and a stable inclusion compound of benzaldehyde having a certain composition and containing a small amount of water is obtained. Moreover, a stable inclusion compound substantially free of water can be obtained by air-drying or drying under reduced pressure the inclusion compound so prepared.

Further, enteric capsules can be formed by enpasulating the inclusion compound of benzaldehyde with an enteric capsule forming material. In general, the enteric capsule contains about 50–200 mg of the inclusion compound. Moreover, tablets can be formed by mixing the inclusion compound of benzaldehyde with appropriate amounts of an excipient such as lactose, refined sucrose, glucose or starch, a binder such as a starch liquid, a gum arabic liquid, a gelatin liquid, a glucose liquid, a refined sucrose liquid or a CMC liquid and a disintegrating agent or other suitable additive to prepare a homogeneous mixture, granulating the mixture, adding a brightener such as magnesium stearate or stearic acid to the granular mixture, and subjecting the resulting granular mixture to compression molding by means of a tableting machine or the like. Still further, tablets may be directly prepared by subjecting a mixture of the inclusion compound of benzaldehyde to compression molding. If a suitable coating material is chosen, enteric tablets can be prepared from these tablets. More specifically, in general, tablets formed by the compression molding are formed into enteric tablets by coating thereon a film of an enteric material such as cellulose acetate phthalate (CAP) or cellulose methacrylate according to a customary method. In general, the enteric tablet contains about 50-200 mg of the inclusion compound.

Examples of pharmaceutical preparations of the composition of the present invention will now be described.

EXAMPLE 1

(Preparation for Injection and Transfusion)

A mixture of 5 g of powdery glucose and 50 mg of commercially available purified benzaldehyde was sterilely distributed in vials and sealed therein. Then, an inert gas such as nitrogen and helium was introduced into vials and they were stored in a cold and dark place. Just before administration, 500 ml of a 0.85% biological sodium chloride solution was added to the powder to form a liquid preparation for intravenous injection. This preparation is administered by intravenous injection or transfusion in an amount of 10 to 500 ml per day, which is appropriately adjusted depending on the disease condition.

EXAMPLE 2

(Preparation for Injection and Transfusion)

A liquid preparation for intravenous injection for mild cases was prepared in the same manner as described in Example 1 except that the amount used of commercially available purified benzaldehyde was changed to 5 mg. The preparation is administered by intravenous injection or transfusion in an amount of 10 to 500 ml per day, which is appropriately adjusted depending on the disease condition.

EXAMPLE 3

(Preparation for Injection and Capsules)

A solution of 30 mg of commercially available purified benzaldehyde in 1 g of refined sesame oil and 100 mg of an aluminum stearate gel was sealed in a vessel, and an inert gas such as nitrogen and helium is introduced in the vessel. The vessel was stored in a cold and dark place. This preparation is divided appropriately and subcutaneously injected in an amount of 1 to 10 ml/day which is appropriately adjusted depending on the disease condition.

Further, the above preparation is distributed into enteric capsules, each containing 0.2 ml of the preparation. The encapsulated preparation is orally administered in an amount of 1 to 10 capsules and 1 to 10 times per day, which is appropriately adjusted depending on the disease condition.

EXAMPLE 4

(Enteric Hard Capsule of Inclusion Compound of Benzaldehyde)

In a saturated aqueous solution of 100 g of commercially available β-cyclodextrin was incorporated 1 g of commercially available purified benzaldehyde, and the mixture was agitated for 5 hours to obtain 80 g of an inclusion compound of benzaldehyde. When this inclusion compound was air-dried, a stable inclusion compound of benzaldehyde substantially free of water was obtained in the form of powder. Then, 100 mg each of the so-obtained inclusion compound was placed in enteric capsules to obtain hard capsules for oral administration. In general, 1 to 10 capsules are orally administered 1 to 10 times per day, while adjusting the dose appropriately depending on the symptoms of the disease.

EXAMPLE 5

(Enteric Tablet of Inclusion Compound of Benzaldehyde)

A homogeneous mixture of 49 parts by weight of the inclusion compound of benzaldehyde prepared in Example 4 with 49 parts by weight of lactose, and 2 parts by weight of magnesium stearate was prepared, and the resulting mixture was formed in 100 mg of tablets by compression molding and then coated with enteric materials.

The so-obtained tablets were subjected to the film coating treatment using a coating solution having the following composition to obtain enteric tablets of the inclusion compound of benzaldehyde:

| | |
|---|---|
| Macrogol 6000 | 8% |
| Cellulose acetate phthalate | 4% |
| Acetone | 50% |
| Ethyl acetate | 20% |
| Ethanol | 18% |

In general, 1 to 20 of the so-prepared tablets are orally administered 1 to 10 times per day, while adjusting the dose appropriately depending on the symptoms of the disease.

What we claim is:

1. A composition, effective against a tumor selected from the group consisting of adenomatous carcinoma, leukaemia, squamous cell carcinoma, sarcoma and lymphosarcoma which comprises an inclusion compound of benzaldehyde in cyclodextrin as the active ingredient, wherein the inclusion compound contains 80 to 100 mg of benzaldehyde per gram of the inclusion compound.

2. A composition according to claim 1 which is in the form of an enteric capsule which contains 50 to 200 mg of said inclusion compound of benzaldehyde in cyclodextrin.

3. A composition according to claim 1, wherein the in the form of an enteric tablet, which contains 50 to 200 mgs of said inclusion compound of benzaldehyde in cyclodextrin.

4. The composition according to claim 1, wherein the cyclodextrin is β or γ cyclodextrin.

5. A method for treating a patient suffering from a tumor selected from the group consisting of adenamatous carcinoma, squamous cell carcinoma, sarcoma, leukaemia and lymphosarcoma, which comprises administering to said patient an amount sufficient to relieve said patient of a composition comprising benzaldehyde as the active ingredient in the form of a transfusion preparation or injection preparation containing 10 to 100 mg of benzaldehyde in 100 ml of the preparation.

6. The method according to claim 5, wherein the preparation is administered in an amount of 10 to 500 ml per day.

7. The method according to claim 5, wherein said composition is in water and is administered in the amount of 0.001-10 mg/kg of body weight once a day.

8. A method for treating a patient suffering from a tumor selected from the group consisting of adenomatous carcinoma, squamous cell carcinoma, sarcoma, leukaemia and lymphosarcoma which comprises administering an amount sufficient to relieve said patient of a composition comprising benzaldehyde as the active ingredient in the form of a capsule containing 5 to 50 mg of benzaldehyde to said patient.

9. The method according to claim 8, wherein the composition is administered in an amount of 1 to 10 capsules and 1 to 10 times per day.

10. The method according to claim 8, wherein the composition is administered orally in the amount of 0.005–50 mg/kg of body weight per day.

11. A method for treating a patient suffering from a tumor selected from the group consisting of adenomatous carcinoma, squamous cell carcinoma, sarcoma, leukaemia and lymphosarcoma which comprises administering an amount sufficient to relieve said patient of a composition comprising an inclusion compound of benzaldehyde in cyclodextrin as the active ingredient to said patient.

12. The method according to claim 11, wherein the inclusion compound of benzaldehyde in cyclodextrin is administered in an amount of 0.5 to 15 g and 1 to 10 times per day.

13. The method according to claim 11, wherein the administering said composition in the form of an enteric capsule or enteric tablet containing 50 to 200 mg of said inclusion compound of benzaldehyde in cyclodextrin to said patient.

14. The method according to claim 13, wherein the composition is administered in an amount of 1 to 10 capsules 1 to 10 times per day.

* * * * *